United States Patent [19]

Stanko

[11] Patent Number: 4,645,764
[45] Date of Patent: * Feb. 24, 1987

[54] METHOD FOR PREVENTING BODY FAT DEPOSITION IN ANIMALS

[75] Inventor: Ronald T. Stanko, Pittsburgh, Pa.

[73] Assignee: Montefiore Hospital, Pittsburgh, Pa.

[ * ] Notice: The portion of the term of this patent subsequent to Sep. 28, 1999 has been disclaimed.

[21] Appl. No.: 736,234

[22] Filed: May 21, 1985

Related U.S. Application Data

[63] Continuation-in-part of Ser. No. 529,403, Sep. 6, 1983, Pat. No. 4,548,937, which is a continuation-in-part of Ser. No. 346,181, Feb. 9, 1982, Pat. No. 4,415,576, which is a continuation-in-part of Ser. No. 249,812, Apr. 1, 1981, Pat. No. 4,351,835.

[51] Int. Cl.$^4$ .................... A61K 31/19; A61K 31/525

[52] U.S. Cl. .................................... 514/251; 514/557; 514/675

[58] Field of Search ................................ 514/251, 557

[56] References Cited

U.S. PATENT DOCUMENTS

| | | | |
|---|---|---|---|
| 4,158,057 | 6/1979 | Stanko | 424/252 |
| 4,351,835 | 9/1982 | Stanko | 424/252 |

*Primary Examiner*—Leonard Schenkman
*Attorney, Agent, or Firm*—Thomas H. Murray; Clifford A. Poff

[57] ABSTRACT

A method for reducing body fat deposition in non-mammals such as chickens by orally administering over a prolonged period a therapeutic mixture of effective amounts of pyruvate and dihydroxyacetone to which may be added riboflavin. The method also increases the total body protein of the non-mammal.

8 Claims, 8 Drawing Figures

METHOD FOR PREVENTING BODY FAT DEPOSITION IN ANIMALS

CROSS REFERENCE TO RELATED APPLICATIONS

This application is a continuation-in-part of application Ser. No. 529,403 filed Sept. 6, 1983 now U.S. Pat. No. 4,548,937 which is a continuation-in-part of application Ser. No. 346,181 filed Feb. 9, 1982 now U.S. Pat. No. 4,415,576 which is a continuation-in-part of application Ser. No. 249,812 filed Apr. 1, 1981 now U.S. Pat. No. 4,351,835.

BACKGROUND OF THE INVENTION

In my U.S. Pat. No. 4,158,057, a method is described for preventing the accumulation of excessive fatty deposits in the livers of mammals. It has long been known that ingestion of ethyl alcohol in mammals, including man, frequently results in the accumulation of excessive fatty deposits in the liver. In many cases, this accumulation tends to become irreversible and may lead to serious consequences, particularly alcohol-induced hepatitis and, ultimately, cirrhosis.

The method described in the aforesaid U.S. Pat. No. 4,158,057 resides in the discovery the excessive fatty deposits in the liver can be reduced or prevented from occurring by administering a therapeutic composition consisting of a mixture of pyruvate and dihydroxyacetone to which may be added riboflavin. These substances are natural metabolites which occur in the body as a result of normal digestive processes. Heretofore, however, there has been no appreciation of any correlation between the accumulation of fatty deposits in the liver, usually due to the ingestion of alcohol, and the accumulation of fat in other parts of the body.

In my U.S. Pat. No. 4,351,835 there is disclosed the surprising discovery, that the mixture of pyruvate and dihydroxyacetone with or without riboflavin when administered for a relatively long period of time, at least 15 days or more, results in a reduction of the rate of hepatic triglyceride generation and body fat deposition for a given diet. The method is thus useful for impeding overweight conditions in mammals, with or without ingestion of ethanol.

Additionally, it has been found that prolonged ingestion of a mixture of pyruvate and dihydroxyacetone, with or without riboflavin, increases the glycogen-storage capabilities of the liver. Stored glycogen is thus increased for subsequent release into the bloodstream. Stored glycogen has been reported to increase the performance and endurance of athletes. It has now been discovered that prolonged ingestion, at least 15 days or more by non-mammals e.g. by chicken, of a mixture of pyruvate and dihydroxyacetone produces a reduction of the rate of hepatic triglyceride generation and body fat deposition for a given diet and increases the glycogen storage capabilities of the liver.

The above and other objects and features of the invention will become apparent from the following detailed description taken in connection with the accompanying drawings which form a part of this specification, and in which.

Figure 1:
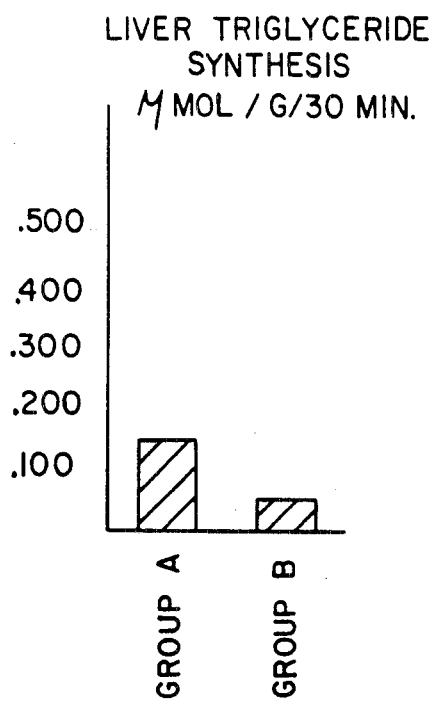
FIG. 1 is a bar graph illustrating the effect liver triglyceride synthesis in mammals of a mixture of pyruvate and dihydroxyacetone for the case where no ethanol is ingested.

To demonstrate the efficiency of the mixture for mammals, a group of rats (Group A) each weighing about 200 grams was fed a standard laboratory diet for a period of 60 days, the diet containing 15% protein, 28% fat and 57% carbohydrate. A second group of rats (Group B) was fed the same diet as Group A except with the addition of a mixture of pyruvate, dihydroxyacetone and riboflavin. The specific mixture comprised 22.5 grams of pyruvate, 22.5 grams of dihydroxyacetone and 2.25 grams of riboflavin per 1000 cubic centimeters of diet. After being on the aforesaid diets for 60 days, each group of rats was injected with radioactive glycerol. About one hour after the injection, the rats were sacrificed, their livers removed, and the radioactive triglyceride generated was determined by chemical analysis. The results are shown in FIG. 1; and it will be noted that the rats in Group B which ingested the mixture of pyruvate, dihydroxyacetone and riboflavin with the same basic diet had a much lower rate of liver triglyceride synthesis. That is, those in Group B had a synthesis rate of about 0.05 millimol per gram per 30 minutes; while those which did not receive the mixture in Group A had a much higher triglyceride synthesis rate of 0.15 millimol per gram per 30 minutes.

Figure 2:
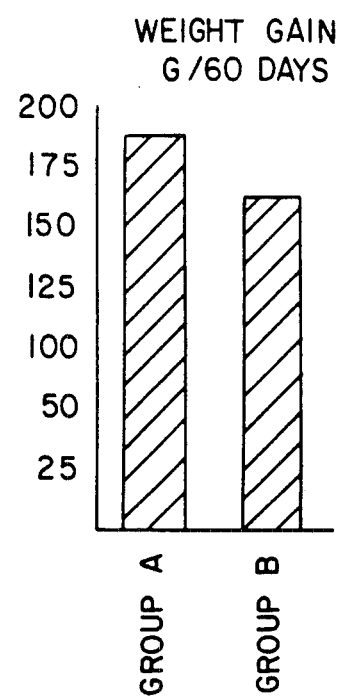
FIG. 2 is a bar graph illustrating the effect in mammals of a mixture of pyruvate and dihydroxyacetone on weight gain for the case where no ethanol is ingested.

More surprising is the effect on weight gain by adding the mixture of pyruvate, dihydroxyacetone and riboflavin to the diet. This is shown in FIG. 2 where, it will be noted, those rats which did not receive the mixture gained almost 190 grams during the 60-day period; whereas those which did receive the agent (Group B) gained only 160 grams. From this it can be concluded that as the rate of triglyceride synthesis decreases, so also does the total weight gain.

Figure 3:
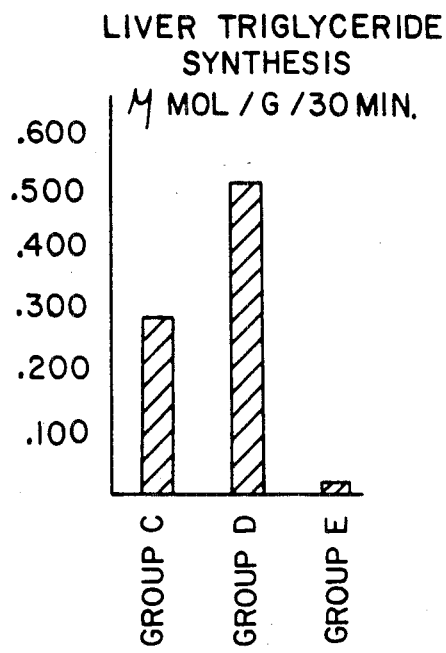
FIG. 3 is a bar graph similar to that of FIG. 2 for the case where ethanol is ingested.
Figure 4:
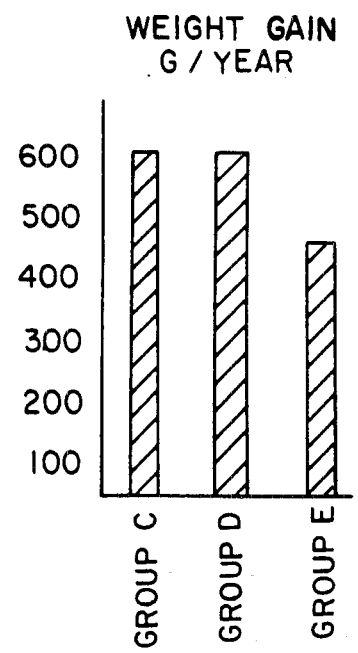
FIG. 4 is a bar graph similar to that of FIG. 2 for the case where ethanol is ingested.
Figure 5:
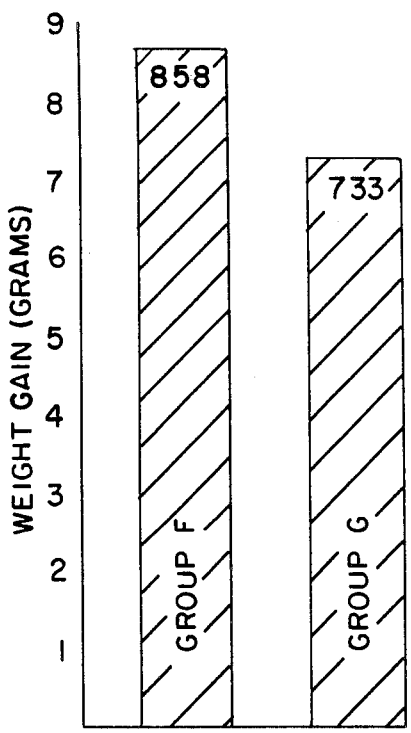
FIGS. 5–8 are bar graphs illustrating the effect of the present invention in a non-mammal.

In another group of experiments extending over a period of one year, rats were divided into three groups ranging from 4 to 8 in number. The first group (Group C) was fed a diet comprising 15% protein, 28% fat and 57% carbohydrate, the same as for Groups A and B. The second group (Group D) received the same diet as Group C except that half of the carbohydrate content of the diet was substituted isocalorically with ethanol. The third group (Group E) received the same diet as Group D containing ethanol but with the addition of 22.5 grams of pyruvate, 22.5 grams of dihydroxyacetone and 2.25 grams of riboflavin per 1000 cubic centimeters of diet. The effect of the rate of triglyceride synthesis is shown in FIG. 3. Note that Group D, which ingested ethanol, has a much higher rate of triglyceride synthesis; whereas Group E which ingested ethanol but at the same time ingested the treating agent of the invention has a much, much lower rate of triglyceride synthesis. The synthesis rate was determined with a radioactive precursor in the same manner as described above in connection with Groups A and B. The effect on weight gain is shown in FIG. 4. Note that Groups C and D had the same weight gain over a year's time, which indicates that ingestion of ethanol and the rate of triglyceride synthesis have very little to do with weight gain. In Group E, however, which had the same diet as Group D, weight gain is significantly lower, being on the order of 450 grams per year as contrasted with 600 grams per year from Groups C and D.

While the treating agent in all cases contained riboflavin, it is believed that this latter agent has a minimal effect on weight gain and that substantially the same effect can be obtained with or without the addition of riboflavin. The quantitative effect on weight gain is dependent upon the dosage; however the dosage is not critical per se. In order to obtain any practical effect as regards weight loss, the agent of the invention should be administered, usually for at least 15 days, until a perceptible weight loss is observed for a given diet. An effective treatment for reducing weight gain in mammals is, therefore, provided utilizing natural metabolites readily available at a relatively low cost.

As is known, the liver, in addition to synthesizing triglycerides, also acts as a storage medium for glycogen. Glycogen is known as the emergency fuel since, unlike fat stores, glycogen is readily available and easy to convert back into glucose. That is, glucose brought to the liver from the intestine via the portal vein is converted to glycogen and stored. As the need arises, glucose is reformed from glycogen and released into the bloodstream. It has been found that by administering the mixture of the invention over a long period of time, the glycogen-storing capability of the liver is increased, accompanied by an increase in the size of the liver. This is shown in the following Table where the glycogen concentration in mg/g of liver tissue and total glycogen are tabulated for the same groups of rate C, D and E described above in connection with FIG. 2, the rate being treated for a period of one year. The livers of four rats in each group were subjected to a standard acid extraction of glycogen after sacrifice.

TABLE

|  | GROUP C | GROUP D | GROUP E |
|---|---|---|---|
|  | Glycogen Concentration* | | |
| Rat No. 1 | 13.2 | 16.5 | 37.1 |
| Rat No. 2 | 17.9 | 13.6 | 31.1 |
| Rat No. 3 | 29.9 | 10.4 | 80.8 |
| Rat No. 4 | 25.6 | 30.2 | 40.3 |
| Average value (mg/g) | 21.65 | 17.6 | 47.3 |
|  | Total Glycogen** | | |
| Rat No. 1 | 227.7 | 275.3 | 841.4 |
| Rat No. 2 | 225.5 | 199.6 | 602.0 |
| Rat No. 3 | 488.8 | 182.8 | 1624.8 |
| Rat No. 4 | 502.0 | 750.1 | 961.9 |
| Average value (mg) | 361 | 351 | 1007 |

*mg of glycogen per gram of liver tissue
**mg of glycogen

While the effect on individual rats in each group varies substantially, it can been seen from the foregoing Table that all rats in Group E which were treated with the mixture of the invention without ingestion of ethanol had much higher glycogen contents than either those in Group D which ingested ethanol without treatment and those in Group C which neither ingested ethanol nor were treated with the mixture of the invention.

For many years athletes have attempted, by eating large amounts of carbohydrate-laden meals, to increase their glycogen stores prior to an athletic event requiring long endurance or sustained high performance. The use of the mixture of the invention appears to increase greatly the glycogen-storage capability of the liver, and disclosed in my U.S. Pat. No. 4,415,576, the mixture also produces an increase in body protein.

Figure 6:
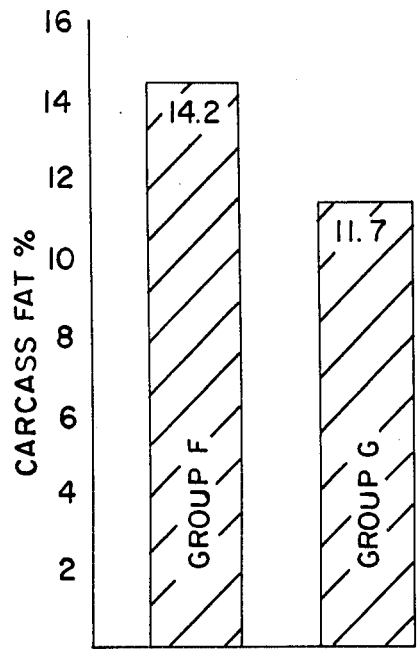
Figure 7:
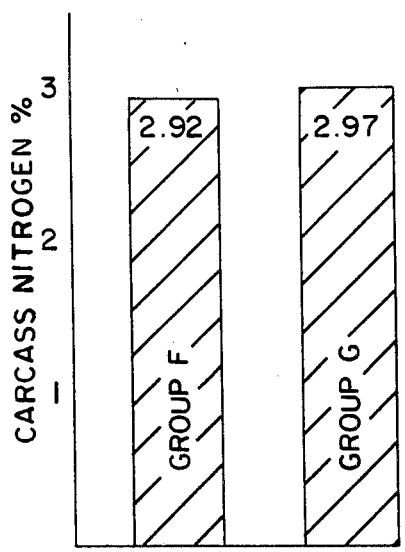

To demonstrate the efficiency of the mixture of the present invention in non-mammals, a group of Hubbard x Hubbard male chickens at an initial age of two days, were pair fed in two groups F and G for a period of 28 days. There were six chickens in each group and control, Group F, was fed a standard diet while the chickens of Group G were fed the same diet except there was added to the diet pyruvate in the amount of 3 percent of the calories and dihydroxyacetone in the amount of 3 percent of the calories. At the end of 28 days, the chickens of each group were sacrificed. The results as shown in FIGS. 5–8 demonstrate that the chickens in Group G which ingested the mixture of pyruvate and dihydroxyacetone with the same basic diet had gained 733 grams as compared with a weight gain of 858 grams by control, Group F. It will be noted again that the chickens in Group G which ingested the mixture of pyruvate and dihydroxyacetone had a significantly lower weight gain. Again there was found a marked inhibition of weight gain in animals, non-mammals was well as mammals, when fed a mixture of pyruvate and dihydroxyacetone. From FIG. 5 it can be again concluded that the lipotropic agent induces a decrease in weight gain while, as shown in FIG. 6, there was a decrease in total body fat in the chickens of Group G as compared with the body fat of the chickens comprising Group F. The total carcass fat in the chickens comprising Group F was 14.2 percent whereas the total carcass fat in the chickens in Group G was only 11.7 percent. Thus, it was found that the percent of body fat decreased by 2.5 percent. From this data, it is concluded that the lipotropic agent not only inhibits weight gain but that the decrease in weight gain is secondary to an inhibition body fat; not protein, water, carbohydrate or minerals. The inhibitory effect of the lipotropic agent on fat metabolism is so great that the body composition actually is changed to the extent that the body fat percent is decreased.

Another finding of the present invention is an increase in the carcass nitrogen store and therefore, also, a small but significant increase to the store of body protein induced by the lipotropic agent. While, this increase is small it is clinically substantial since the protein concentration of the body is small and only a modest increase in protein is helpful. This is especially important in certain patients, specifically weight-watchers or body builders.

Figure 8:
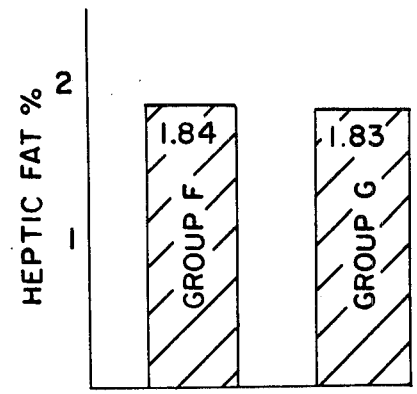

To further demonstrate the efficiency of the invention, as can been seen from FIG. 8, the group of six chickens comprising Group F were found to experience a 0.01 percent greater heptic fat deposition than the chickens comprising Group G. The animals of Group G experienced a 1.83 percent heptic fat deposition and the animals of Group F experienced a 1.84 percent heptic fat deposition. The surprising effect by the addition of a mixture of pyruvate and dihydroxyacetone to the diet of non-mammals was determined on an average per chicken basis where p 0.01.

Although the invention has been shown in connection with certain specific embodiments, it will be readily apparent to those skilled in the art that various changes can be made to suit requirements without departing from the spirit and scope of the invention.

I claim as my invention:

1. A method for controlling the deposition of body fat in a living being which comprises administering orally to said living being a therapeutic mixture of pyruvate and dihydroxyacetone in an effective amount to induce a weight loss or to reduce an expected weight gain from a given diet.

2. The method of claim 1 in which said mixture also includes riboflavin.

3. The method of claim 1 wherein said mixture is administered for at least 15 days.

4. The method according to claim 1 wherein said mixture is administered for 60 days.

5. The method according to claim 1 wherein said body fat deposition in said living being is effectively reduced by administering said mixture.

6. The method according to claim 1 wherein body protein of said living being is increased.

7. A method for inhibiting body fat while increasing body protein concentration in a living being which comprises administering orally to said living being effective amounts of therapeutic mixture of pyruvate and dihydroxyacetone for a given diet.

8. The method according to claim 7 wherein said mixture is administered for at least 15 days.

* * * * *